(12) United States Patent
Shirley (10) Patent No.: US 7,896,828 B1
(45) Date of Patent: Mar. 1, 2011

(54) ORTHOSIS

(76) Inventor: Frank Shirley, Norwell, MA (US)

( * ) Notice: Subject to any disclaimer, the term of this patent is extended or adjusted under 35 U.S.C. 154(b) by 91 days.

(21) Appl. No.: 12/288,840

(22) Filed: Oct. 23, 2008

Related U.S. Application Data

(62) Division of application No. 11/343,549, filed on Jan. 31, 2006, now Pat. No. 7,476,208.

(60) Provisional application No. 60/653,614, filed on Feb. 16, 2005.

(51) Int. Cl.
*A61F 5/00* (2006.01)
(52) U.S. Cl. .................. 602/27; 602/5; 602/6; 602/7; 602/23
(58) Field of Classification Search ............. 602/27–29, 602/5–8, 60–64; D24/190, 192
See application file for complete search history.

(56) References Cited

U.S. PATENT DOCUMENTS 4,693,239 A * 9/1987 Clover, Jr. .................... 602/27
4,869,267 A 9/1989 Grim et al.
5,501,659 A * 3/1996 Morris et al. ................. 602/27
5,657,767 A 8/1997 Nelson et al.
5,899,872 A 5/1999 Gilmour

* cited by examiner

*Primary Examiner*—Kim M Lewis
(74) *Attorney, Agent, or Firm*—David M. Driscoll, Esq.

(57) ABSTRACT

An ankle support that is adapted to securely hold the lower leg, ankle and foot of a wearer so as to provide reparative support thereof and an associated method of fabrication thereof. The ankle support includes an outer shell formed of a rigid material that conforms substantially to the configuration of the wearer and including an upper portion for at least partially surrounding the lower leg, an intermediate portion about the ankle and a lower portion that at least partially supports the foot; an inner liner formed of a flexible and conformable material and including an upper portion for at least partially surrounding the lower leg, an intermediate portion about the ankle and a lower portion that at least partially supports the foot and an interlocking mechanism including cooperating and interlocking members of the respective outer shell and inner liner that assist in retaining the inner liner within the outer shell.

4 Claims, 15 Drawing Sheets

ORTHOSIS

RELATED APPLICATION

This application is a divisional of U.S. Ser. No. 11/343,549 filed on Jan. 31, 2006 now U.S. Pat. No. 7,476,208 which claims priority to U.S. Provisional Application Ser. No. 60/653,614 filed on Feb. 16, 2005 and each of which is incorporated by reference herein in its entirety.

TECHNICAL FIELD

The present invention relates in general to an orthosis device preferably for the support of the foot. More particularly, the present invention relates to a method of fabricating an ankle brace used as an orthosis.

BACKGROUND OF THE INVENTION

A typical orthosis relies primarily upon strapping to secure the orthosis about the foot or ankle. The strapping may include a single strap or multiple straps, sometimes used in a figure eight strap arrangement. Typical strap arrangements are disclosed in the following U.S. Pat. Nos. 4,869,267; 5,501,659; 5,657,767 and 5,899,872. These types of strap arrangements have shown to be ineffective and result in the heel of the foot pulling up and out from the desired position of the foot in the orthosis.

One of the challenges to the orthotist is the patient that has tone and heel chord tightness. It is desired with this type patient to maintain the ankle foot complex in the desired, usually 90 degree position, to aid in the ability to either ambulate more efficiently or to not aggravate any type of deformity that is currently present.

Accordingly, it is an object of the present invention to provide an improved orthosis for securely maintaining and holding the ankle complex in the desired position.

Another object of the present invention is to provide an orthosis that has the characteristic of maintaining the desired position of the ankle through the use of a two-part brace structure that employs a male-female locking mechanism.

Another object of the present invention is to provide an improved method of fabricating a foot orthosis.

SUMMARY OF THE INVENTION

In accordance with the present invention there is provided an ankle support that is adapted to securely hold the lower leg, ankle and foot of a wearer so as to provide reparative support thereof. The ankle support comprises an outer shell formed of a rigid material that conforms substantially to the configuration of the wearer and including an upper portion for at least partially surrounding the lower leg, an intermediate portion about the ankle and a lower portion that at least partially supports the foot; an inner liner formed of a flexible and conformable material and including an upper portion for at least partially surrounding the lower leg, an intermediate portion about the ankle and a lower portion that at least partially supports the foot; and an interlocking mechanism including cooperating and interlocking members of the respective outer shell and inner liner that assist in retaining the inner liner within the outer shell.

In accordance with other aspects of the present invention the interlocking mechanism may comprise at least one outwardly directed projection on the inner liner that is engagable with an aligned opening in the outer shell; preferably a pair of oppositely disposed projections are provided for respective engagement with a pair of oppositely disposed openings in the outer shell; each of the projections may be in the form of a horizontally disposed ridge and each opening may be substantially rectangular and longer in the horizontal direction to mate with the like shaped projection; each projection may be disposed so that the rear end thereof is on the order of an inch from the rear of the liner and the bottom side thereof is on the order of one inch from the bottom of the liner; and the interlocking mechanism may comprise a protruding element on one of the outer shell and inner liner and an open element on the other of the outer shell and inner liner.

In accordance with another aspect of the present invention there is provided a method of fabricating an ankle brace constructed of an outer rigid shell and an inner flexible liner. This method comprises the steps of: providing a mold of the wearers lower leg, ankle and foot; forming a locking protuberance on the outer surface of the mold; constructing the inner flexible liner by forming a flexible and conformable plastic material over the mold while forming a liner projection from the locking protuberance; constructing the outer rigid shell by forming a plastic material over the mold while forming an opening in alignment with the locking protuberance; separating the outer shell and the inner liner from the mold; and engaging the inner liner into the outer shell while interlocking the locking protuberance on the inner liner with the opening in the outer shell.

In accordance with other aspects of the method of the present invention the interlocking protuberance may be formed by providing an insert received in a passage of the mold, said insert extending from both sides of said mold to form opposite locking ends; the locking protuberance may be positioned so that the rear end thereof is on the order of an inch from the rear of the mold and the bottom side thereof is on the order of one inch from the bottom of the mold; the step of constructing the inner liner preferably includes forming a pair of oppositely disposed projections using a vacuum forming procedure; the step of constructing the inner liner preferably includes forming a projection that is rectangular in shape and that extends with its longer edge in a horizontal plane; the projection may be positioned so that the rear end thereof is on the order of an inch from the rear of the liner and the bottom side thereof is on the order of one inch from the bottom of the liner; the step of constructing the outer shell may include forming a plastic material over the flexible and conformable plastic material of the inner liner including forming a projection on the outer shell, and removing the thus formed projection to make the opening; may further include forming a pair of oppositely disposed projections on the outer shell and removing the thus formed projections to provide a pair of oppositely disposed openings, and forming an intermediate liner over the mold followed by the formation of the outer shell over the intermediate liner.

In accordance with still other aspects of the present invention there is provided a method of fabricating an ankle brace constructed of an outer rigid shell and an inner flexible liner. This method comprises the steps of: providing a mold of the wearers lower leg, ankle and foot; forming a locking protuberance on the outer surface of the mold; constructing the inner flexible liner by forming a flexible and conformable plastic material over the mold while forming a liner projection from the locking protuberance; constructing the outer rigid shell by forming a plastic material over the inner liner material while forming a shell projection from the locking protuberance; separating the outer shell and the inner liner from the mold; removing the shell projection so as to form an opening for positioning in alignment with said liner projection; and engaging the inner liner into the outer shell while interlocking the projection on the inner liner with the opening in the outer shell.

In accordance with other aspects of the present invention the step of constructing the inner liner preferably includes forming a pair of oppositely disposed projections, and the step of constructing the outer shell includes forming a pair of shell projections; and further including removing both shell projections to form oppositely disposed openings for respective engagement with the liner projections.

In accordance with another aspect of the present invention there is provided a method of fabricating an ankle brace constructed of an outer rigid shell and an inner flexible liner. This method comprises the steps of: providing a mold of the wearers lower leg, ankle and foot; forming a locking protuberance on the outer surface of the mold; constructing the inner flexible liner by forming a flexible and conformable plastic material over the mold while forming a liner projection from the locking protuberance; removing the inner liner from the mold; providing an intermediate liner disposed over the mold; constructing the outer rigid shell by forming a plastic material over the intermediate liner while forming a shell projection; removing the outer shell from the intermediate liner; removing the shell projection so as to form an opening for positioning in alignment with the inner liner projection; and engaging the inner liner into the outer shell while interlocking the projection on the inner liner with the opening in the outer shell. The step of constructing the inner flexible liner may include forming a pair of oppositely disposed projections, and the step of constructing the outer shell may include forming a pair of shell projections.

DESCRIPTION OF THE DRAWINGS

Numerous other objects, features and advantages of the present invention should now become apparent upon a reading of the following detailed description taken in conjunction with the accompanying drawings, in which.

DETAILED DESCRIPTION

Figure 1:
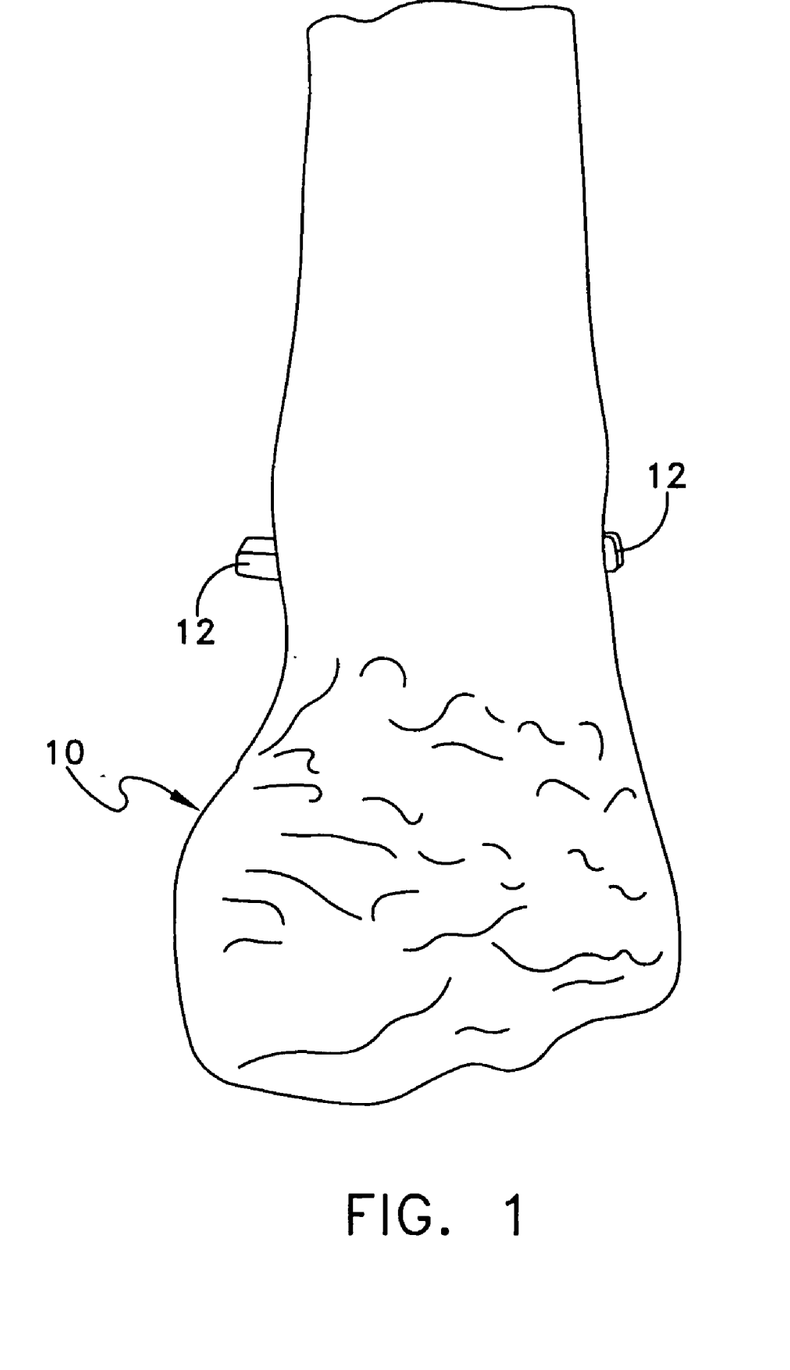
FIG. 1 is a front view of a positive plaster mold as modified in accordance with the present invention.
Figure 2:
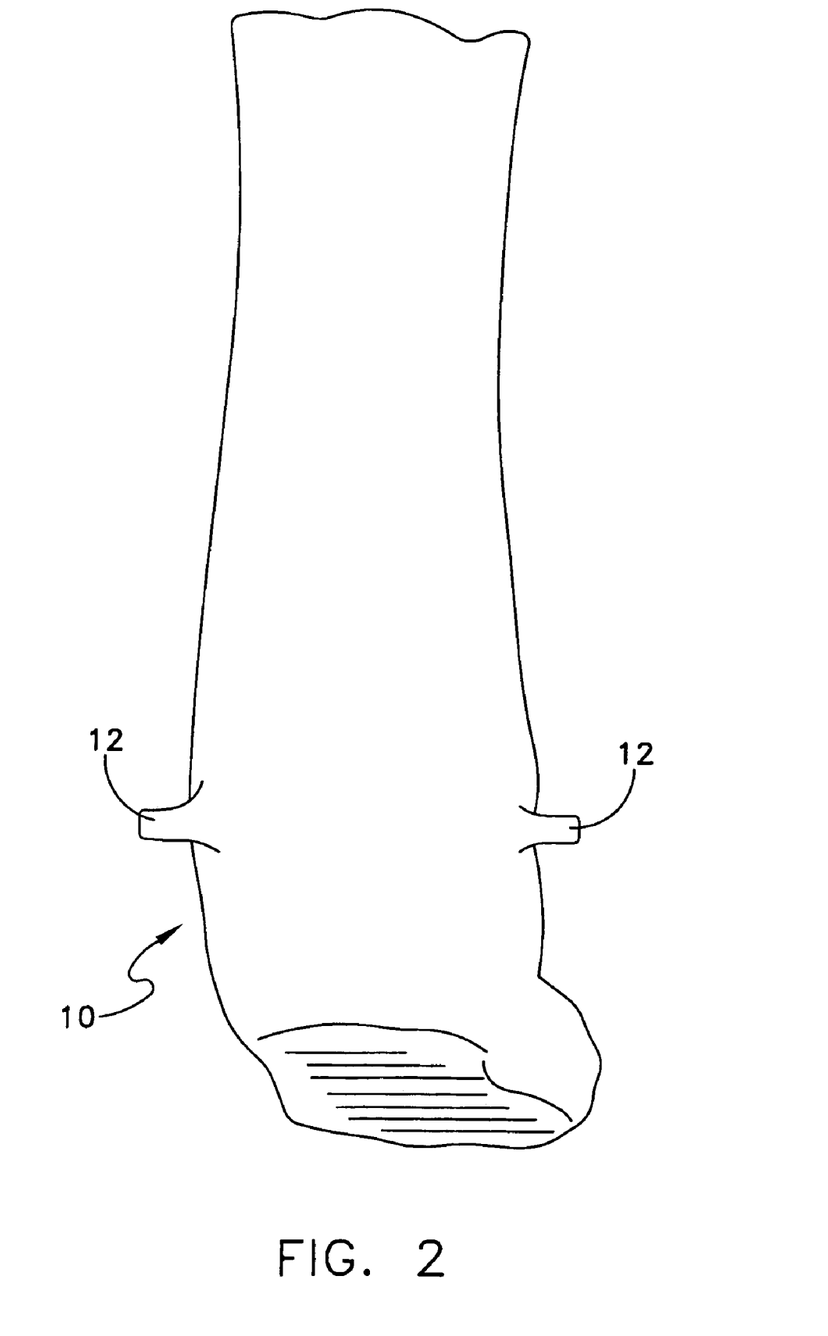
FIG. 2 is a rear view of the mold of FIG. 1.
Figure 3:
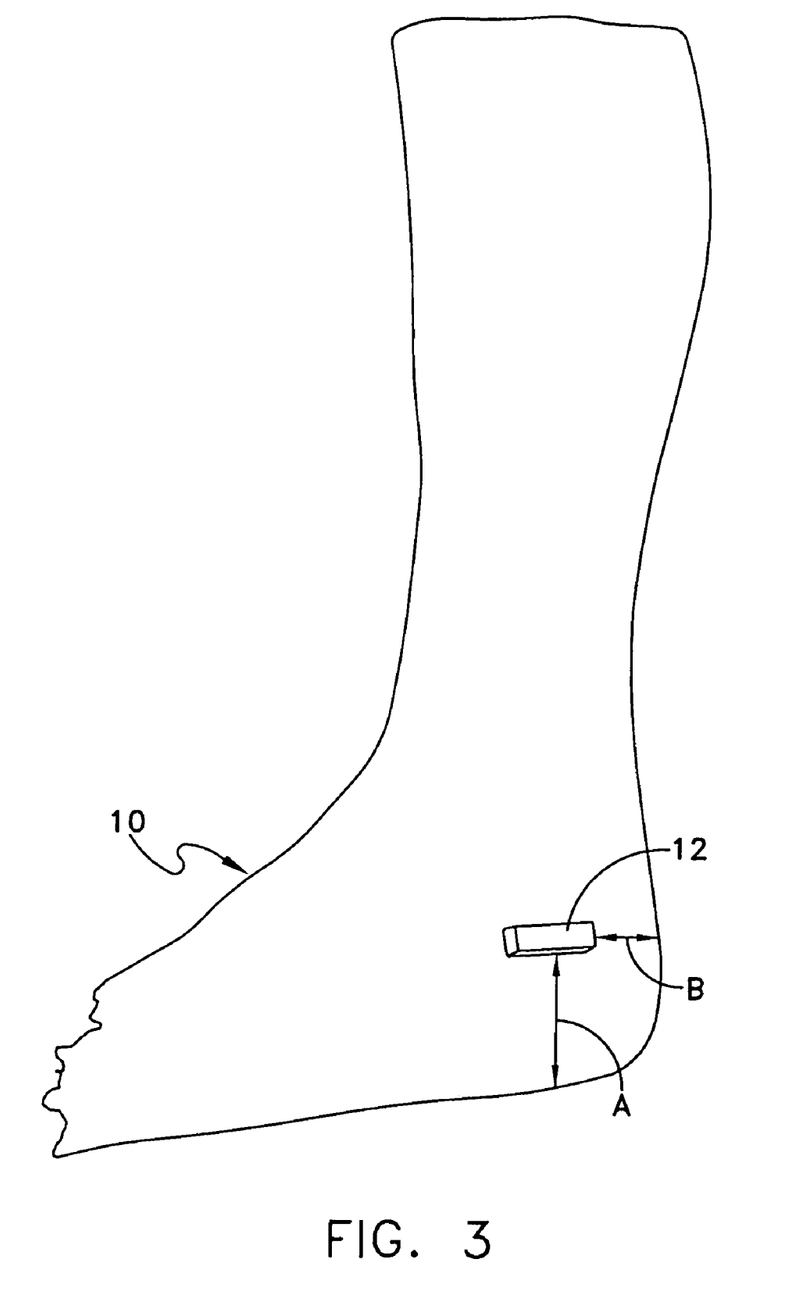
FIG. 3 is a partial side view of the mold of FIG. 1 illustrating the addition of a protuberance for registration purposes.

Reference is now made to FIGS. 1-3 showing a positive mold that has been made of the wearer's foot. FIG. 1 is a front view of a positive plaster mold as modified in accordance with the present invention. FIG. 2 is a rear view of the mold of FIG. 1. FIG. 3 is a partial side view of the mold of FIG. 1 illustrating the addition of a protuberance or projection for registration purposes.

The orthosis is made from an impression taken either with casting material or with the use of a cad-cam device. The positive impression is then modified adding additional relief for boney prominences and smoothing any irregularities from the casting or carving. The locking mechanism is achieved primarily by providing a somewhat elongated projection that is disposed distal to the medial and lateral malleous. This projection is preferably positioned in a horizontal plane and may be about ⅛ inch wide and approximately ¾ of an inch in length.

Refer now to FIGS. 1-3 showing respective front, rear and side view of positive impression or mold 10. A pair of projections 12 is shown, for example, in FIG. 2 extending from opposite sides of the mold. In the drawings the projections are shown somewhat squared, however, they are preferably formed with rounded edges. The side view of FIG. 3 shows one of the projections 12. This projection 12 is extending substantially in a horizontal plane along its length. The projection 12 is positioned below and rearward of the position of the ankle bone. The rear end of the projection is positioned the dimension B, about 1.25 inch from the very rear of the mold or in a range of from ¾ of an inch to 1¾ inch. The dimension B may be on the order of one inch. The bottom of the projection 12 is located by the dimension A about 1.25 inch from the bottom of the mold or in a range of from ¾ of an inch to 1¾ inch. The dimension A may be on the order of 1.25 inch.

Figure 4:
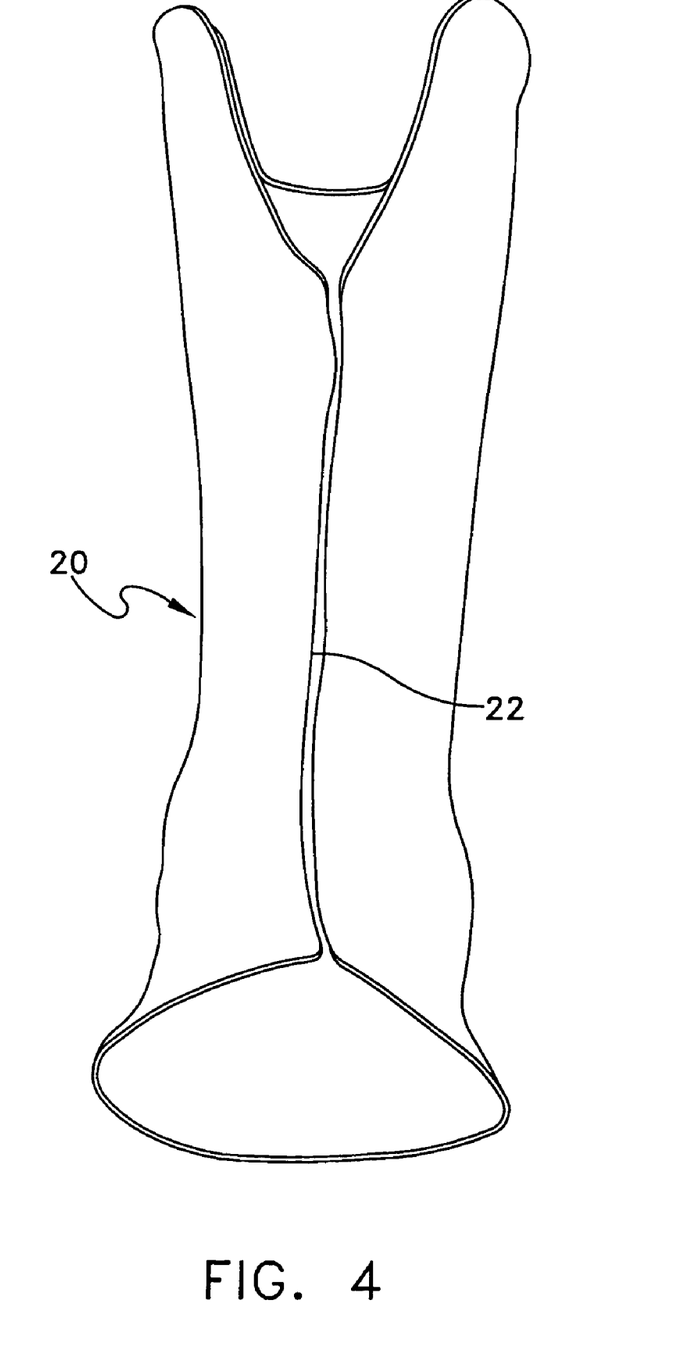
FIG. 4 is a front view of the inner liner as formed from the mold.
Figure 5:
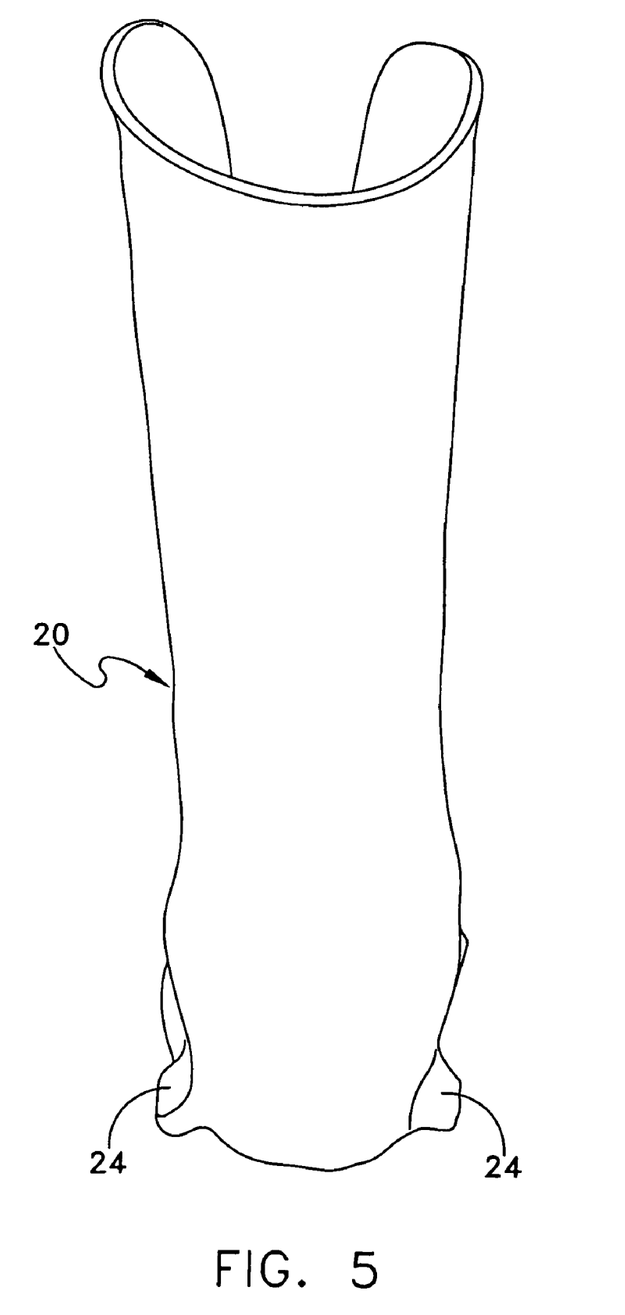
FIG. 5 is a rear view of the liner of FIG. 4 illustrating the formation of a projection or protuberance on the inner liner.
Figure 6:
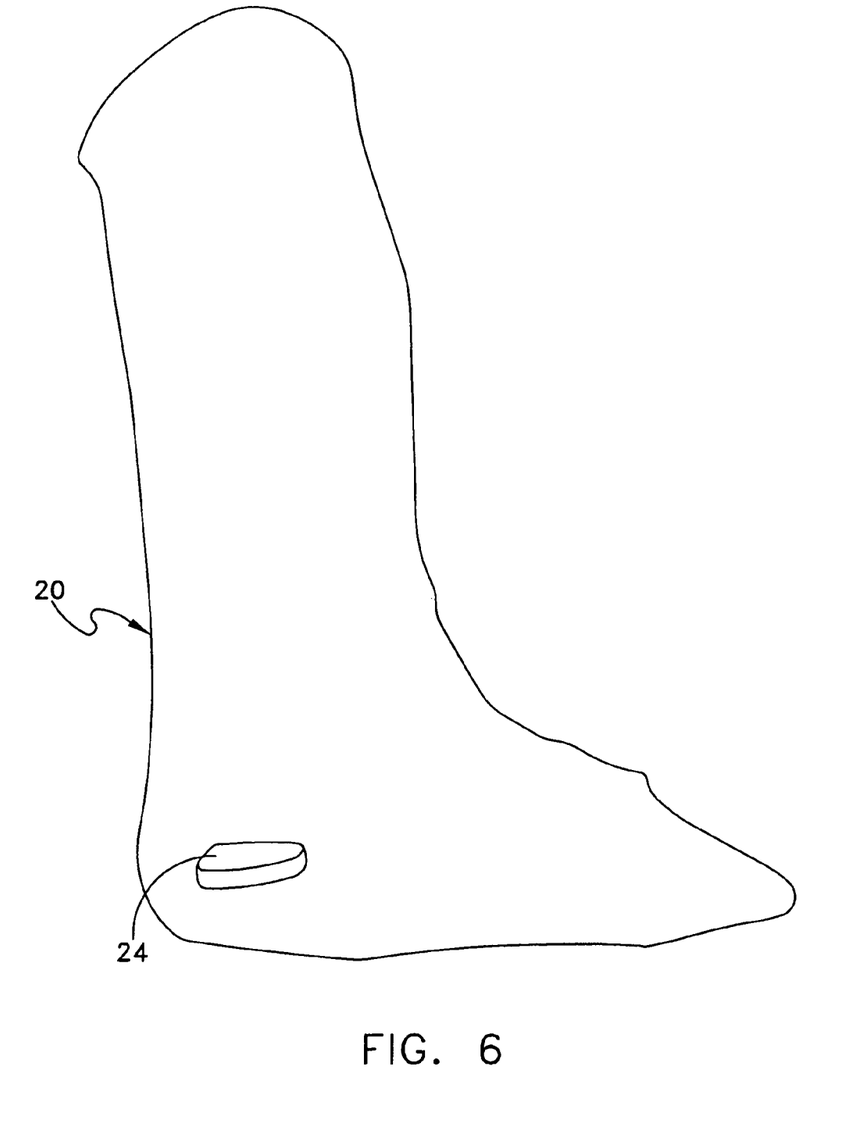
FIG. 6 is a side view of the inner liner of FIGS. 4 and 5.
Figure 7:
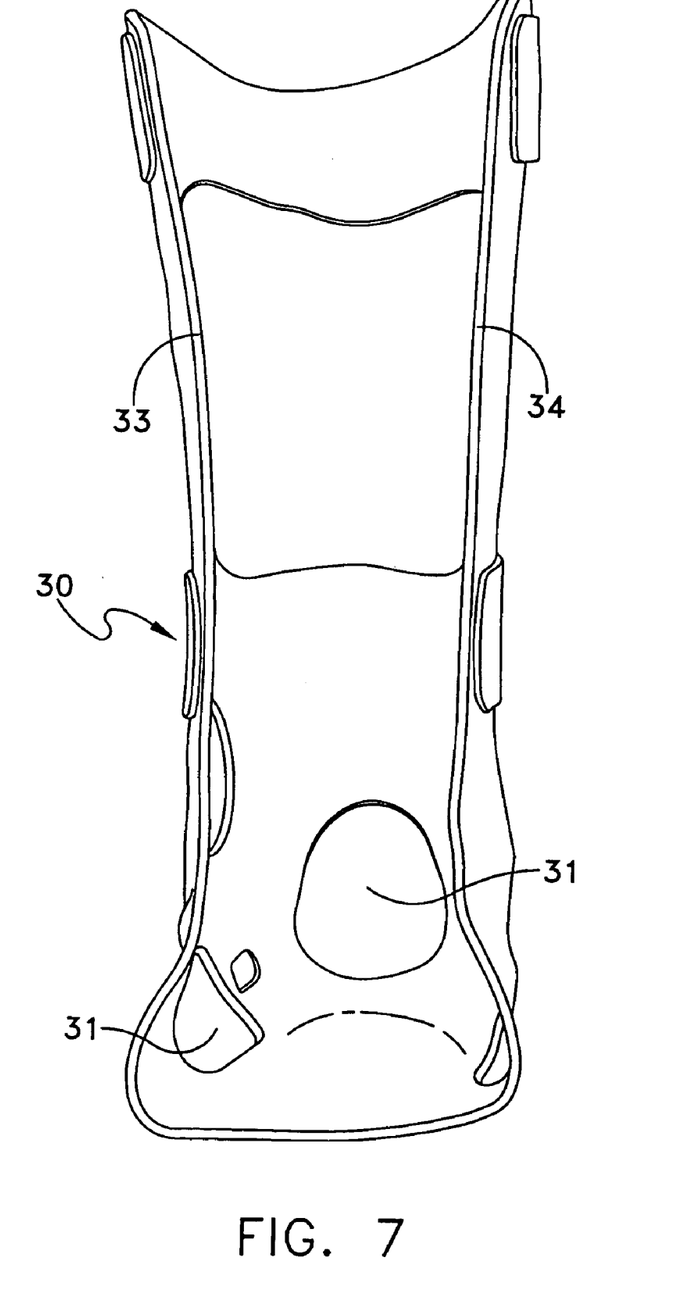
FIG. 7 is a front view of the outer shell alone as formed from the mold with portions thereof removed.
Figure 8:
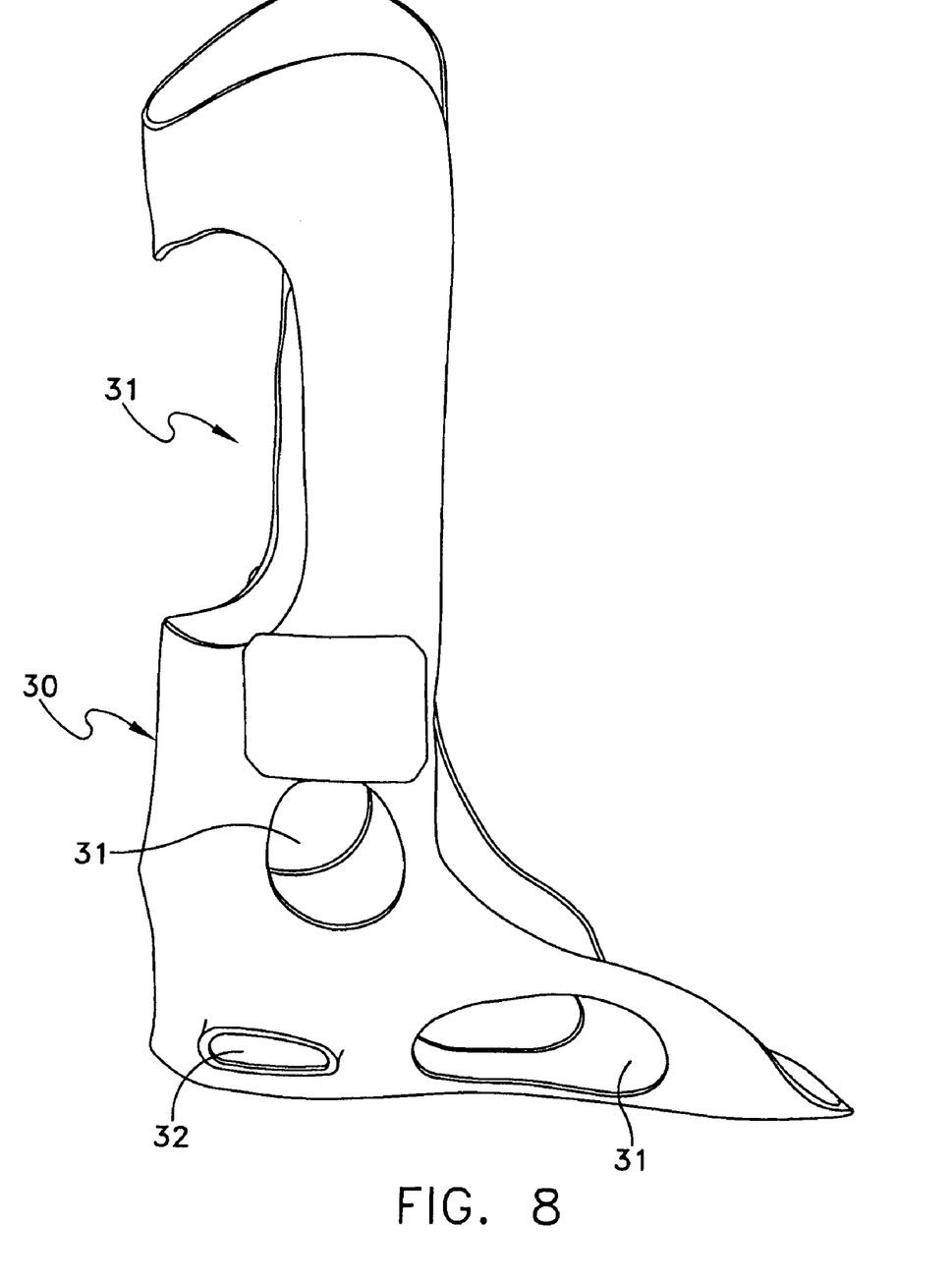
FIG. 8 is a side view of the outer shell of FIG. 7 illustrating the formation of a recess or slot for alignment with the inner liner projection.
Figure 9:
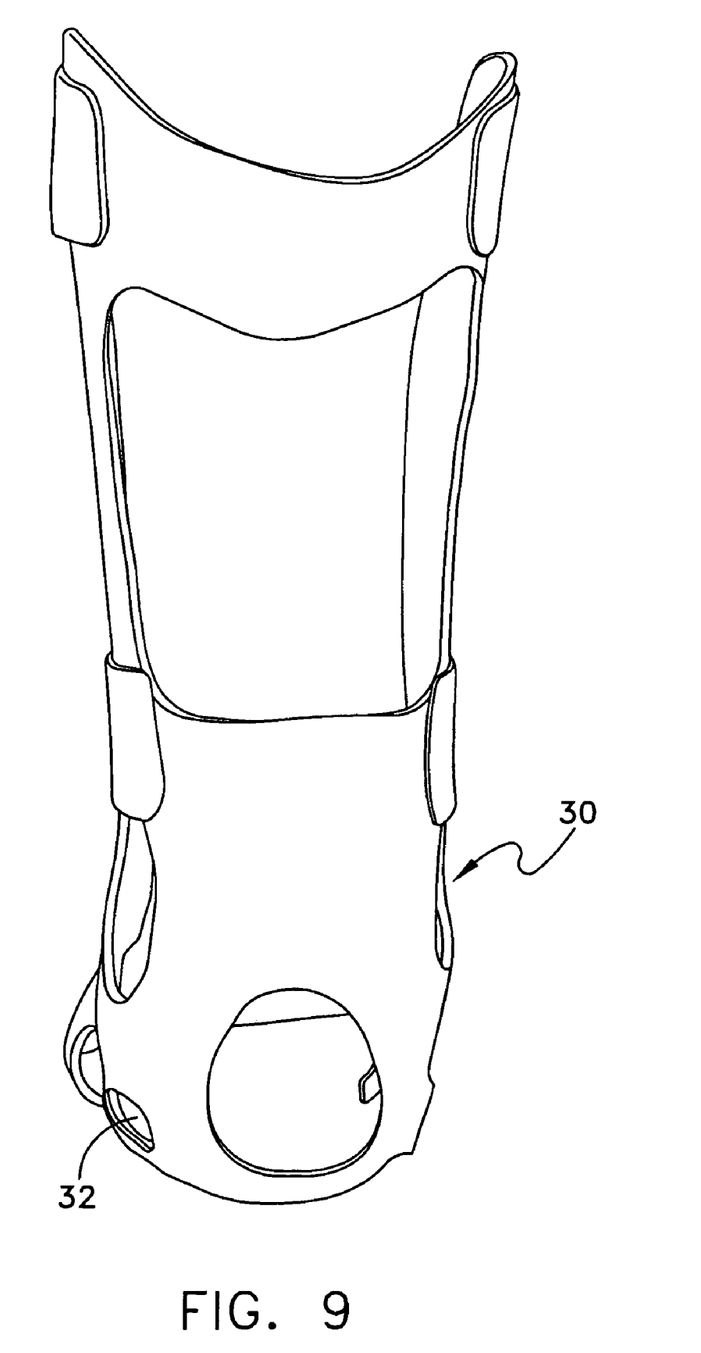
FIG. 9 is a rear view of the outer shell of FIGS. 7 and 8.

Once the positive impression is formed then one is ready to commence the fabrication of the support device of the present invention. The mold illustrated in FIGS. 1-3 is used to form both the outer shell and the inner liner that together form the support structure. FIGS. 4-6 illustrate the inner liner which is constructed of a more flexible material, while the outer shell which is illustrated in FIGS. 7-9, is constructed of a more rigid material, both of an appropriate plastic material.

The positive impression is positioned so that layers of a proflex thermal plastic material can be vacuum formed thereover. A ⅛ inch thick sheet of thermoplastic material that is appropriately sized for the particular mold is heated and drape molded and then vacuum formed onto the positive impression making sure to clearly define the male portion of the locking mechanism or locking projection. This would be formed by the part of the thermoplastic material that is draped over and vacuum formed against the projections 12 illustrated in FIGS. 1-3. This first disposed layer that is vacuum formed is for forming the flexible inner liner of the orthosis. In this regard refer to FIGS. 4-6 showing the liner 20 with oppositely disposed projections 24 and a forward disposed parting line 22.

In the molding and vacuum forming method the next step is to provide a thermal plastic rigid material which may also have a thickness on the order of ⅛ inch or slightly greater than that. The thickness of the rigid material depends upon the size of the mold. The thermoplastic rigid material is to form the outer shell and is made of a material that once formed becomes relatively rigid. The inner liner, on the other hand, is made of a thermoplastic material that, once formed, remains flexible. The thermoplastic rigid material is then heated and vacuum formed over the previously formed piece of proflex thermoplastic material. After these steps, the two layers are then left to cool. When the plastics have cooled sufficiently, then they may be individually removed from the mold in order to produce the respective flexible inner liner and rigid outer shell.

FIGS. 4-6 illustrate the final configuration of the inner liner 20. The front view of FIG. 4 shows the parting line 22 that defines a front gap that is useful in fitting the inner liner to the wearer's foot. FIGS. 5 and 6 illustrate the projection 24 that is formed by the first layer having been vacuum formed over the mold 10 with its projection 12. In other words the projection 12 of the mold forms the projection 24 of the inner liner 20. This provides part of the lock down mechanism previously referenced. As indicated previously, each of these projections 24 correspond substantially in size to the projections 12 and thus may be three-fourth inch by one-eighth inch projections one-quarter of an inch distal to the medial and lateral malleous. In some of the drawings this is illustrated schematically and may not be in the exact position as placed. FIG. 6 also shows the projections 24. As indicated previously, a sheet of thermoplastic material is vacuum molded about the casting to clearly define the male portion, namely the projection 24 of the lock down mechanism.

The interior proflex portion, namely the flexible liner 20, of the orthosis is removed from the more rigid shell of the orthosis. The rigid thermoplastic portion of the orthosis is then modified by outlining those areas which are the areas of the boney prominences as well as the heel section. Removal of these areas allows for further relief from pressure areas and will thus aid in the locking of the more flexible inner lining into the outer rigid shell. Once these areas are removed and smoothed, the anterior portion of the rigid outer shell of the orthosis may be trimmed. Refer to FIGS. 7-9 for a showing of the rigid shell 30. Removed areas are shown, for example, at 31 in FIGS. 7 and 8. FIGS. 7-9 also show the opening 32 that is formed as to be described hereinafter. It is also noted that the outer shell has a substantial opening at its front end between edges 33 and 34 while the flexible liner 20 has close adjacent edges as indicated at the parting line 22 in FIG. 4.

When the outer rigid shell is formed over the inner lining of the mold the mold projection also forms a projection on the outer surface of the outer shell in the position where the projection 24 is on the inner liner such as illustrated in FIG. 6. The projections on the outer shell are sanded or ground off substantially level with the surface of the shell so as to form the opening 32, as depicted in, for example, FIG. 8.

Once the flexible liner has been removed from the mold it may also be trimmed so as to be as anterior as possible. As indicated previously, this layer is quite flexible and thus readily conforms to the patient's leg and is able to be encompassed about essentially the entire leg structure. This holds the leg in the desired position. Once the flexible inner liner has been trimmed and the openings have been provided in the outer shell, the inner liner may be placed into the outer shell and the projections 24 of the liner will extend into the open slots or opening 32 of the rigid exterior shell thus providing essentially one integral interlocked orthosis.

Reference is now made to FIGS. 10-13 for an illustration of various view showing the liner disposed within the shell. Also shown are straps 40. These may be Velcro® (hook and loop fastener) straps that are applied at their ends at the anterior proximal portion of the rigid shell. In, for example, FIG. 10 two straps 40 are shown one at the top of the orthosis and the other just above the ankle.

The sequence of use of the orthosis is as follows. First, the foot is inserted into the flexible inner shell so that the ankle is in a comfortable neutral position. Next, with the leg in the liner, the liner is moved from the front into the outer rigid shell slowly. Pressure is then applied in a downward manner and exerted to force the projections on the liner into the apertures or openings of the outer shell. This provides the firm interlock between the liner and shell. The straps may then be fastened in the manner illustrated in, for example, FIG. 10. Once this is accomplished, the person's ankle complex is now held down in the desired position and is firmly locked in position primarily by the use of the lock-down mechanism of projections and corresponding openings or apertures.

In order to remove the foot from the orthosis, the shoe is removed and the straps, are unfastened. The foot is slid out without separating the two parts of the orthosis. To remove the inner flexible liner, the liner is then pinched at the ankle area toward the center until the projections come out of their respective openings in the rigid outer shell and the liner is then easily removed.

Reference is made to the drawings and in particular to FIGS. 1-13 for one embodiment in accordance with the method of the present invention. FIGS. 1-3 show the mold. FIGS. 4-6 illustrate the inner shell which is constructed of a more flexible material. FIGS. 7-9 illustrate the outer shell which is constructed of a more rigid material. Both the inner liner and the shell are constructed of a thermal plastic material. These elements of the orthosis may be constructed of polypropylene of polyethylene products. Each of these elements when draped in the mold may have a thickness on the order of ⅛ inch.

Reference to FIG. 6 clearly illustrates one of the two oppositely disposed projections 24. This provides part of the lock down mechanism previously referenced. As indicated previously, each of these projections may be about ⅛ inch wide by approximately ¾ inch long and is disposed distal to the medial and lateral malleous. As also indicated previously, a sheet of thermoplastic material is vacuum molded about the casting to clearly define the male portion or projection 12 of the lock down mechanism.

The outer shell is illustrated in FIGS. 7-9. This is formed of a thermoplastic rigid material with the thickness being dictated by the size of the leg. This layer is heated and vacuum formed over the previously formed piece that defines the inner liner. These two layers are then left to cool. When the plastics have cooled, they can be removed from the mold in order to produce the finished product.

The interior proflex portion of the orthosis is removed from the more rigid portion of the orthosis to provide the interlocking slot or slot opening or gap 32 such as illustrated in FIG. 8. It is the protrusion 24 that will be adapted to interlock with this slot 32. The slot is provided by grinding away the protrusion that is left from the molding process. This is ground away, of course, only on the outer rigid shell. Also, as illustrated in, for example FIG. 8 other areas are shown as removed where they are boney prominences.

Figure 10:
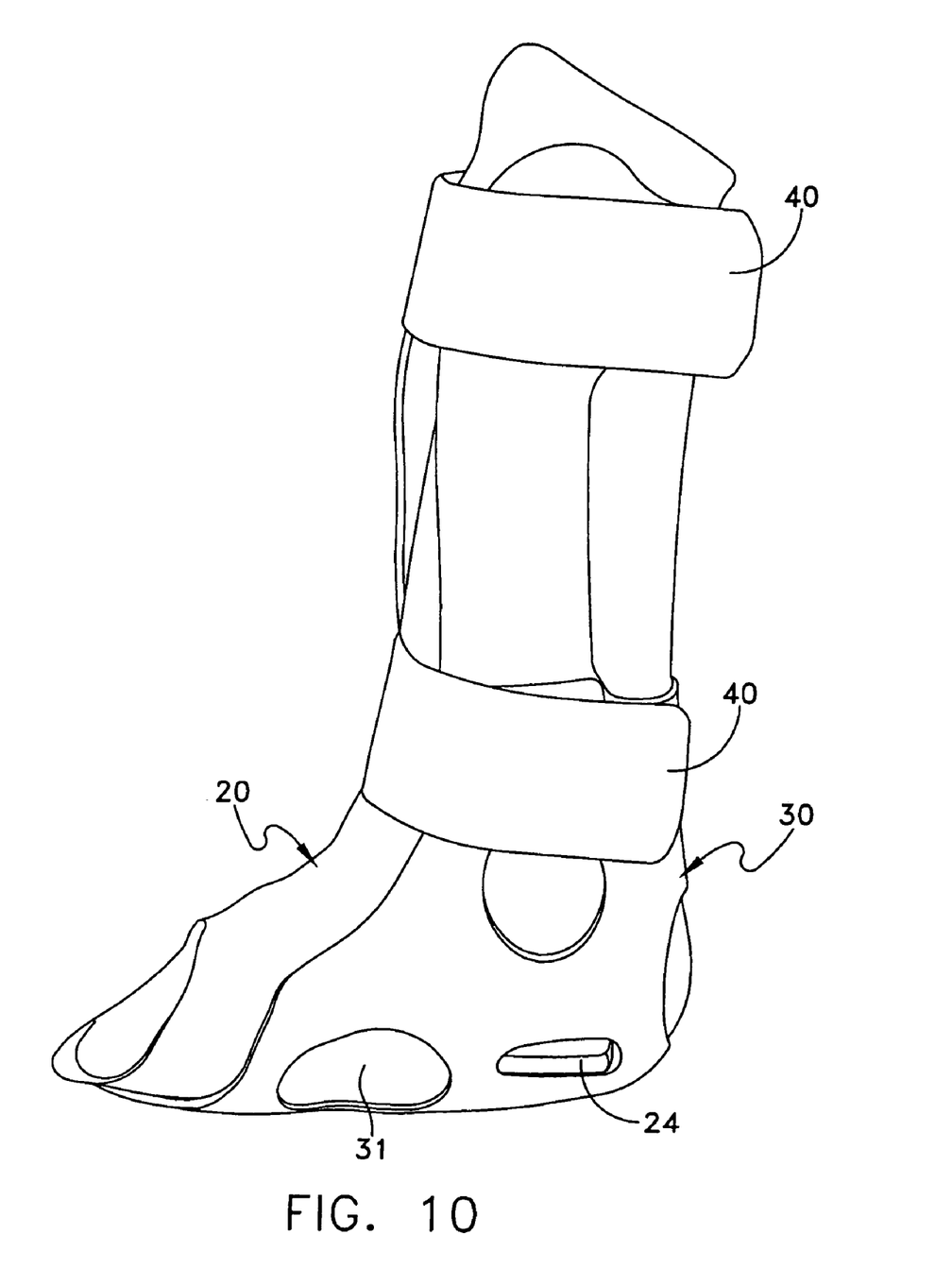
FIG. 10 is a side view of the combined orthosis including the inner liner, outer shell and holding straps.
Figure 11:
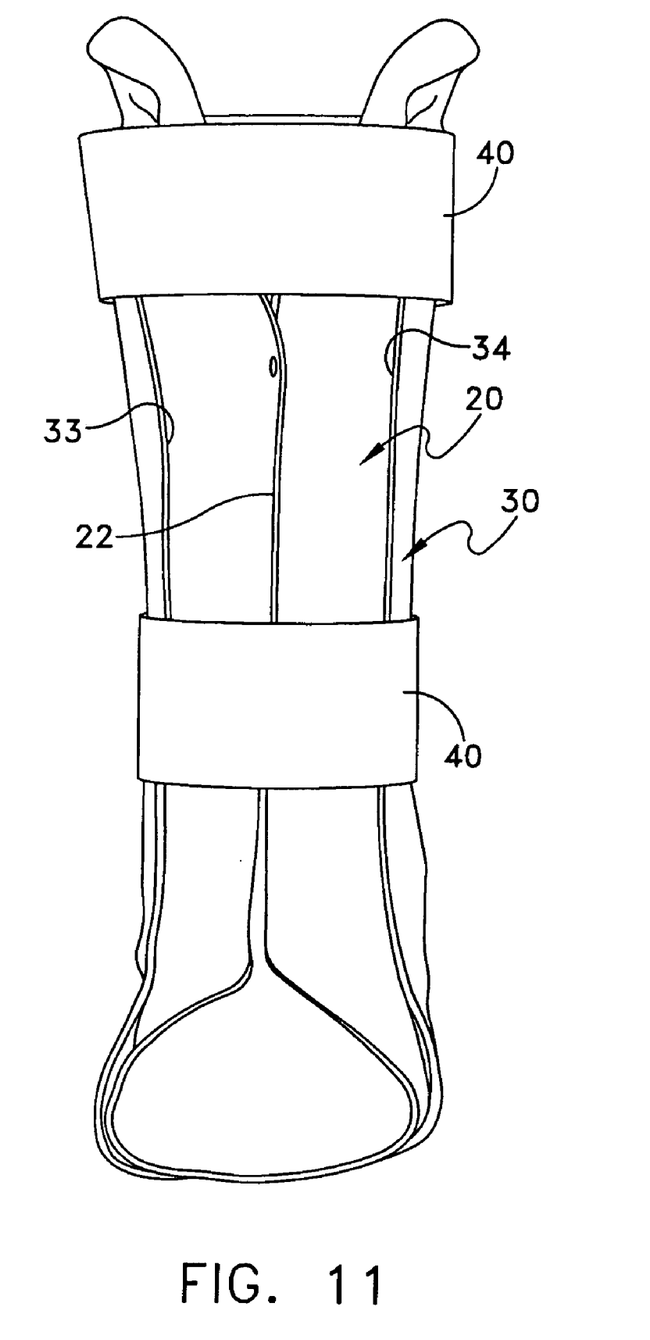
FIG. 11 is a front view of the orthosis of FIG. 10.
Figure 12:
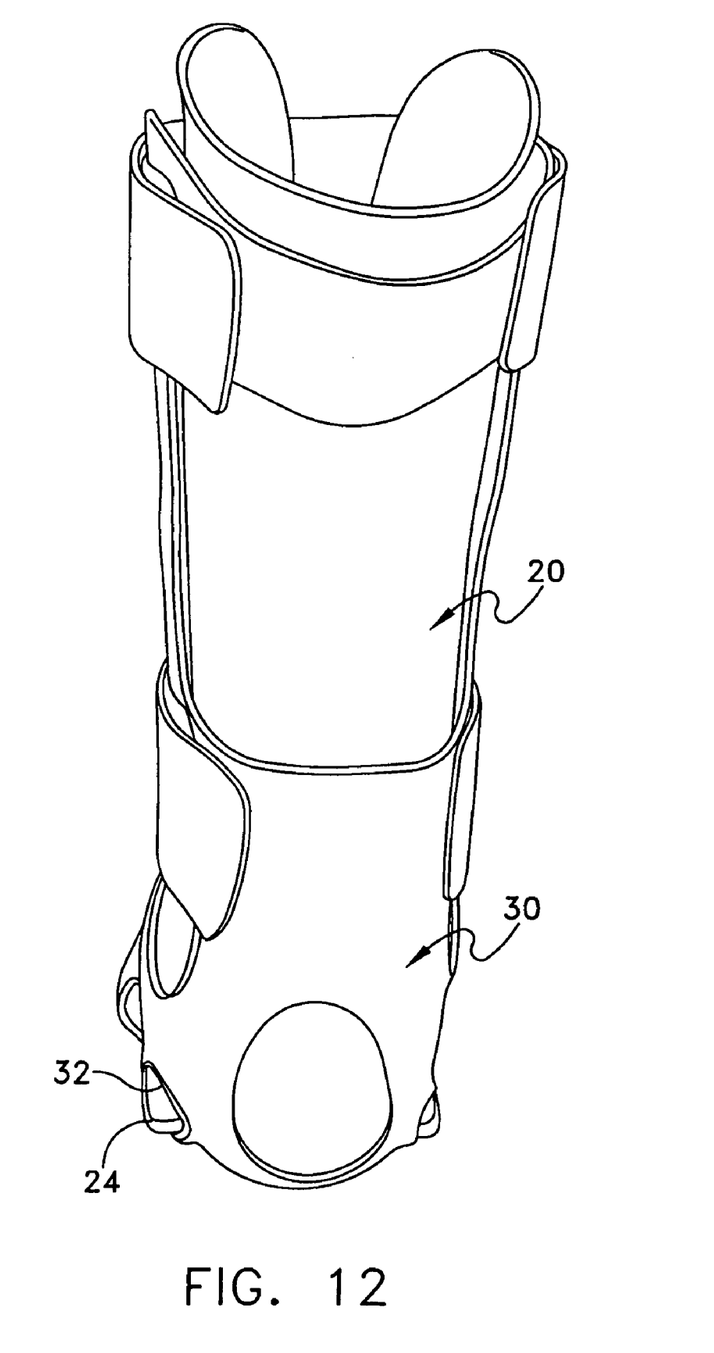
FIG. 12 is a rear view of the orthosis shown in FIGS. 10 and 11.
Figure 13:
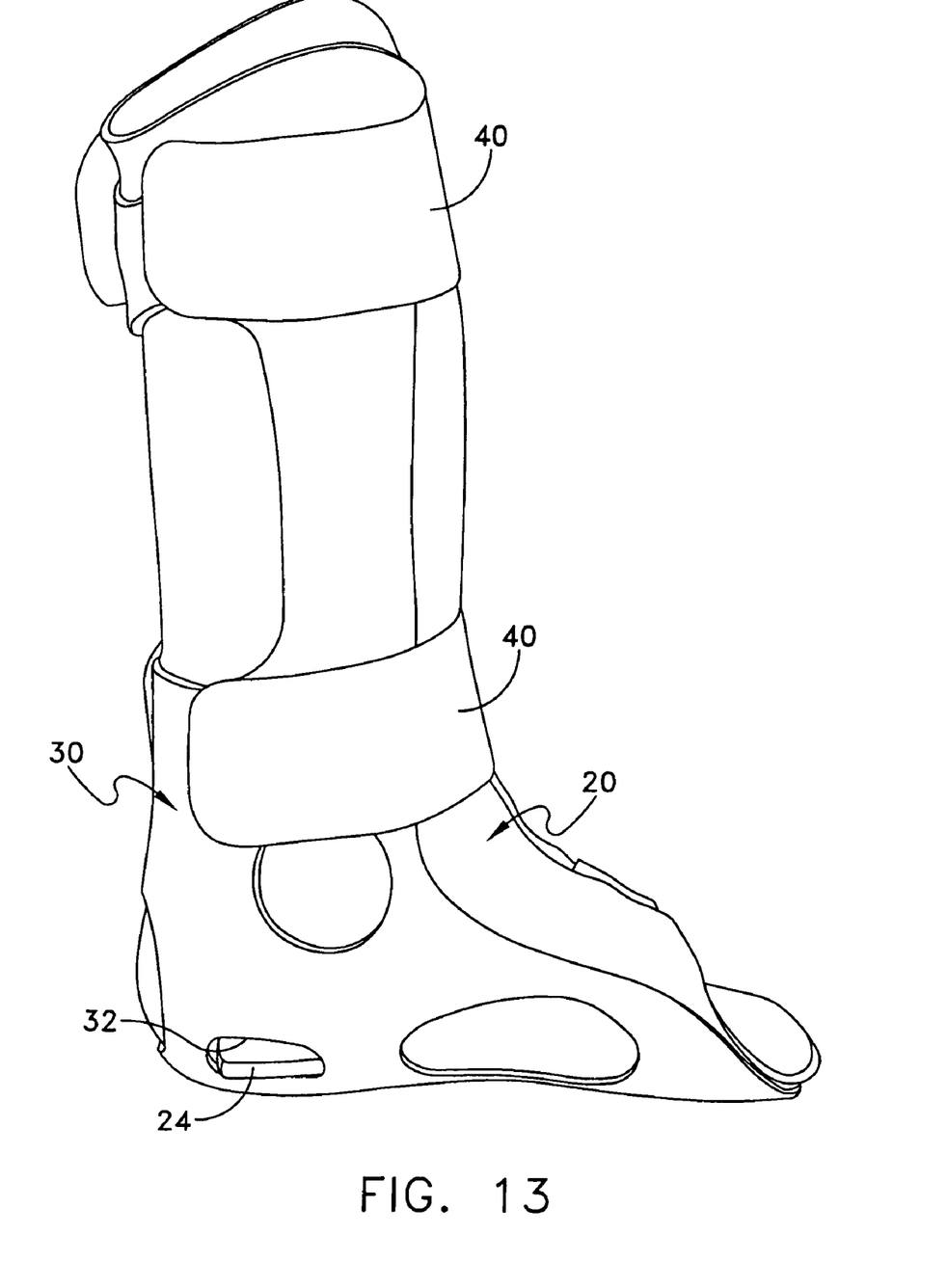
FIG. 13 is an opposite side view of the orthosis.

Refer now also to FIGS. 10-13. FIG. 10 is a side view of the combined orthosis including the inner liner, outer shell and holding straps. FIG. 11 is a front view of the orthosis of FIG. 10. FIG. 12 is a rear view of the orthosis shown in FIGS. 10 and 11. FIG. 13 is an opposite side view of the orthosis. These various views illustrate the inner liner of now inserted into the outer shell. For example, FIG. 12 shows the inner shell with its protrusion 24 interlocking in the slot or gap 32. Refer also to FIG. 13 which clearly illustrates the manner in which the interlocking occurs between the protrusion 24 of the inner liner and the slot 32 in the outer more rigid shell. Refer also to FIG. 11 that shows the manner in which the inner shell is meant to join at the front thereof as at the parting line 22. On the other hand, the outer rigid shell is open as illustrated in FIG. 11 between edges 33 and 34. This enables the foot to be inserted rearwardly into the rigid outer shell with ease. FIG. 11 also illustrates the straps 40 that may be coupled by Velcro® (hook and loop fastener) so as to secure the orthosis about the wearer's foot.

Figure 14:
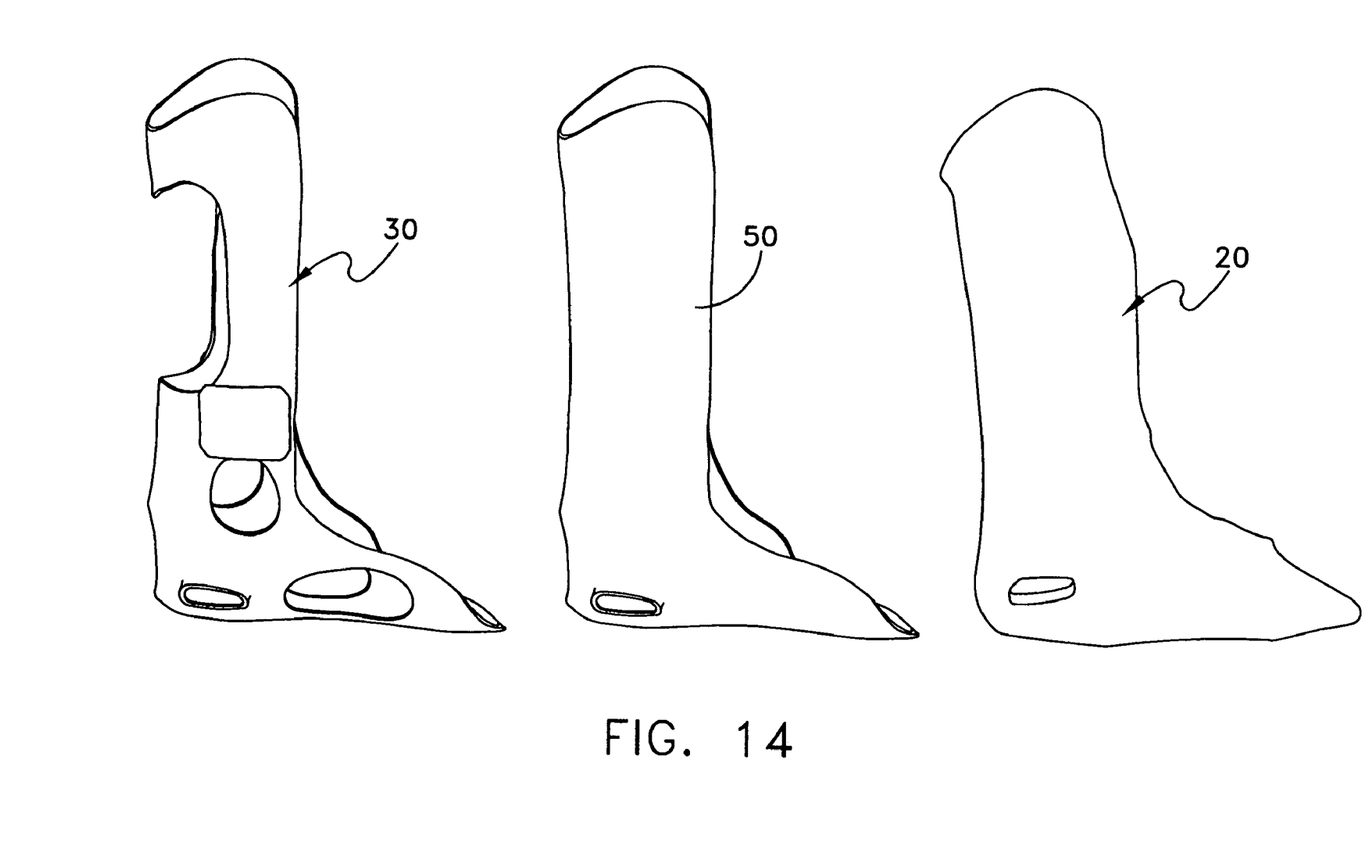
FIG. 14 is an illustration for an alternate method using a "dummy" liner.
Figure 15:
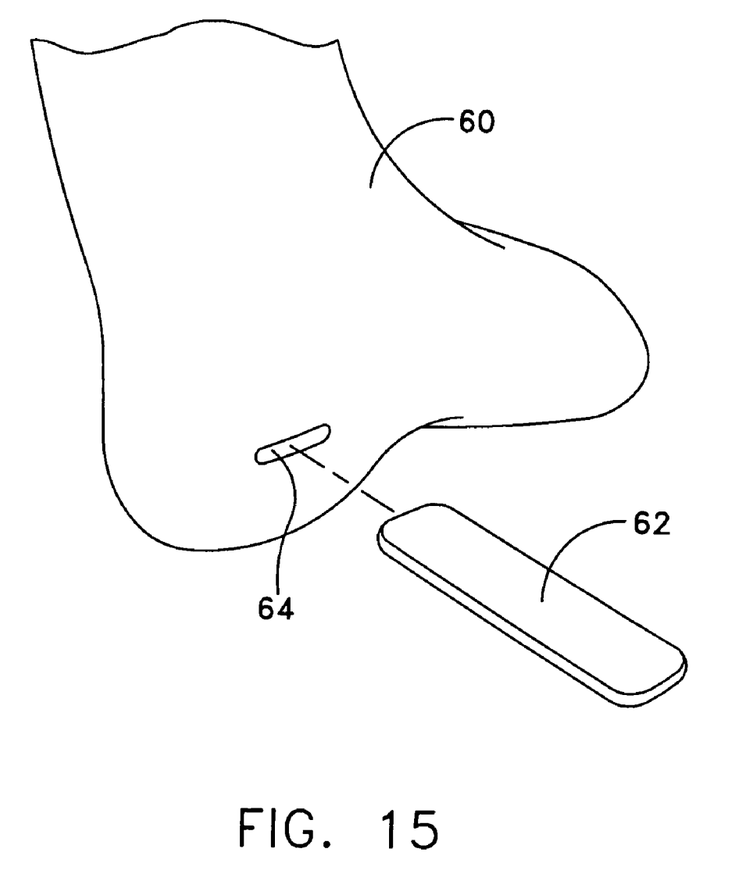
FIG. 15 illustrates an alternate way of forming the protuberance in the mold.

Reference is also now made to an alternate method illustrated in FIG. 14 and also an alternate form of constructing the projection in the casting as illustrated in FIG. 15. It has been found that there might be some difficulty in removing the outer shell from the inner lining and thus in accordance with one method of the present invention in addition to the inner liner 20 and the outer shell 30 depicted in FIG. 14 there may also be provided a dummy liner 50. In accordance with this method, the inner liner is formed about the mold in the manner as previously described. Then the liner is permitted to cool and then removed from the mold. Thereafter, a dummy layer is inserted of a material similar to the material of the outer shell. This layer is also conformed to the mold and thus has a pair of projections formed in the same manner as with the inner liner. This is vacuum formed about the mold and preferably has a thickness the same as that of the liner 20. The more rigid thermoplastic material for the shell 30 is then heat and vacuum formed over the dummy liner material. After the molding process is complete, because the materials of the liner 50 and the shell 30 are similar, they can be more easily removed from each other.

Reference is also now made to FIG. 15 for an illustration of one way of providing the projection on the mold. FIG. 15 shows the basic mold 60 and a removable stick 62 that may be tightly inserted into an opening 64 in the mold. The stick 62 will extend from either side of the mold in a manner similar to that illustrated in FIG. 2, extending about the same length from either side of the mold. The ends of the stick thus form the respective projections and may each have a depth of about one-eighth to three-eighth inch from the mold surface. The stick 62 may be disposable.

In the second step of this molding process, per FIG. 14, it is also easier to remove the two mold members 30 and 50 and then simply grind away the protuberance or projection on the outer shell 30 to form the aforementioned gap 32. The dummy liner 50 can be discarded. During this grinding process part of the stick may also be ground away to make it easier to remove the components from the mold.

Having now described a limited number of embodiments of the present invention it should be apparent to those skilled in the art that numerous other embodiments and modifications thereof are contemplated as falling within the scope of the present invention, as defined by the appended claims.

What is claimed is:

1. An ankle support that is adapted to securely hold the lower leg, ankle and foot of a wearer so as to provide reparative support thereof, said ankle support comprising:
    an outer shell formed of a rigid material that conforms substantially to the configuration of the wearer and including an upper portion for at least partially surrounding the lower leg, an intermediate portion about the ankle and a lower portion that at least partially supports the foot;
    an inner liner formed of a flexible and conformable material and including an upper portion for at least partially surrounding the lower leg, an intermediate portion about the ankle and a lower portion that at least partially supports the foot;
    and an interlocking mechanism including cooperating and interlocking members of the respective outer shell and inner liner that assist in retaining the inner liner within the outer shell;
    wherein said interlocking mechanism comprises at least one outwardly directed projection on said inner liner that is engagable with an opening in the outer shell.

2. The ankle support of claim 1 including a pair of oppositely disposed projections for respective engagement with a pair of oppositely disposed openings in the outer shell.

3. The ankle support of claim 2 wherein each of the projections are in the form of a horizontally disposed ridge and each opening is substantially rectangular and longer in the horizontal direction to mate with the like shaped projection.

4. The ankle support of claim 3 wherein each projection is disposed so that the rear end thereof is on the order of an inch from the rear of the liner and the bottom side thereof is on the order of one inch from the bottom of the liner.

* * * * *